United States Patent
Peterson et al.

(10) Patent No.: US 11,376,348 B2
(45) Date of Patent: *Jul. 5, 2022

(54) ALLOGENEIC MICROVASCULAR TISSUE FOR SOFT TISSUE TREATMENTS

(71) Applicant: MICROVASCULAR TISSUES, INC, San Diego, CA (US)

(72) Inventors: Dale R. Peterson, Carlsbad, CA (US); Richard B. Emmitt, Oldwick, NJ (US)

(73) Assignee: Micro Vascular Tissues, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,090

(22) Filed: Oct. 5, 2018

(65) Prior Publication Data

US 2019/0038805 A1  Feb. 7, 2019

Related U.S. Application Data

(63) Continuation of application No. 14/698,763, filed on Apr. 28, 2015, now Pat. No. 10,137,224, which is a continuation of application No. 13/423,171, filed on Mar. 17, 2012, now Pat. No. 9,044,430.

(60) Provisional application No. 61/454,367, filed on Mar. 18, 2011.

(51) Int. Cl.
| | |
|---|---|
| *A61L 27/36* | (2006.01) |
| *A61K 35/35* | (2015.01) |
| *C12N 5/077* | (2010.01) |
| *A61L 27/38* | (2006.01) |
| *A61K 35/28* | (2015.01) |
| *A61K 35/12* | (2015.01) |
| *A61L 27/54* | (2006.01) |
| *A61L 27/56* | (2006.01) |

(52) U.S. Cl.
CPC .......... *A61L 27/3662* (2013.01); *A61K 35/12* (2013.01); *A61K 35/28* (2013.01); *A61K 35/35* (2013.01); *A61L 27/3604* (2013.01); *A61L 27/3625* (2013.01); *A61L 27/3683* (2013.01); *A61L 27/3687* (2013.01); *A61L 27/3691* (2013.01); *A61L 27/3834* (2013.01); *A61L 27/54* (2013.01); *A61L 27/56* (2013.01); *C12N 5/0653* (2013.01); *A61L 2300/64* (2013.01); *A61L 2430/06* (2013.01); *A61L 2430/10* (2013.01)

(58) Field of Classification Search
CPC ........ A61K 35/28; A61K 35/35; A61K 35/12; A61L 27/3662; A61L 2430/10; A61L 2430/06; A61L 2300/64; A61L 27/56; A61L 27/54; A61L 27/3691; A61L 27/3687; A61L 27/3625; A61L 27/3604; C12N 5/0653
USPC ...................................................... 424/93.7
See application file for complete search history.

(56) References Cited

U.S. PATENT DOCUMENTS

| | | |
|---|---|---|
| 5,358,931 A | 10/1994 | Rubinsky |
| 5,656,498 A | 8/1997 | Iijima et al. |
| 5,730,933 A | 3/1998 | Peterson |
| 5,786,207 A | 7/1998 | Katz et al. |
| 6,200,606 B1 | 3/2001 | Peterson et al. |
| 7,125,856 B1 | 10/2006 | Isner |
| 7,270,946 B2 | 9/2007 | Brockbank |
| 7,560,276 B2 | 7/2009 | Harmon et al. |
| 7,659,111 B2 | 2/2010 | Rubinsky et al. |
| 8,048,671 B2 | 11/2011 | Hendriks et al. |
| 8,119,398 B2 | 2/2012 | Sayre et al. |
| 9,044,430 B2 | 6/2015 | Peterson et al. |
| 9,713,629 B2 | 7/2017 | Peterson et al. |
| 9,872,937 B2 | 1/2018 | Peterson et al. |
| 10,137,224 B2 | 11/2018 | Peterson et al. |
| 2006/0147430 A1 | 7/2006 | Sayre et al. |
| 2007/0274960 A1 | 11/2007 | Harman et al. |
| 2007/0292401 A1 | 12/2007 | Harmon et al. |
| 2008/0033572 A1 | 2/2008 | D'Antonio et al. |
| 2008/0286323 A1 | 11/2008 | Tornoe et al. |
| 2009/0324558 A1 | 12/2009 | Attawia et al. |
| 2010/0068245 A1 | 3/2010 | Manders |
| 2010/0124563 A1 | 5/2010 | Coleman et al. |
| 2010/0178681 A1 | 7/2010 | Lee et al. |
| 2010/0256692 A1 | 10/2010 | Kang et al. |
| 2012/0164113 A1 | 6/2012 | Victor |
| 2012/0183673 A1 | 7/2012 | Arsan et al. |
| 2014/0017787 A1 | 1/2014 | Betancourt |
| 2014/0255357 A1 | 9/2014 | Burt |
| 2015/0218506 A1 | 8/2015 | Nash et al. |
| 2015/0231183 A1 | 8/2015 | Peterson et al. |
| 2017/0360845 A1 | 12/2017 | Peterson et al. |

(Continued)

FOREIGN PATENT DOCUMENTS

| | | |
|---|---|---|
| CN | 101505796 A | 8/2009 |
| CN | 101757691 | 6/2010 |

(Continued)

OTHER PUBLICATIONS

Aslan, H. et al., Osteogenic differentiation of noncultured immunoisolated bone marrow-derived CD105+ cells. *Stem Cells*, 24(7):1728-1737. (2006).

(Continued)

*Primary Examiner* — Jennifer M. H. Tichy
(74) *Attorney, Agent, or Firm* — Cooley LLP

(57) ABSTRACT

Disclosed are products and methods for treating soft tissue injuries. The provided methods include the production of processed or cryopreserved microvascular tissue. Also provided are products and methods of using processed or cryopreserved microvascular tissue for the treatment of soft tissue injuries.

6 Claims, 5 Drawing Sheets

(56) References Cited

U.S. PATENT DOCUMENTS

| | | | |
|---|---|---|---|
| 2018/0133371 | A1 | 5/2018 | Peterson et al. |
| 2018/0161379 | A1 | 6/2018 | Peterson et al. |
| 2019/0038805 | A1 | 2/2019 | Peterson et al. |
| 2019/0091261 | A1 | 3/2019 | Peterson et al. |

FOREIGN PATENT DOCUMENTS

| | | |
|---|---|---|
| EP | 0668013 A2 | 8/1995 |
| JP | 2010-240379 | 10/2010 |
| WO | WO 1997/026326 | 7/1997 |
| WO | WO 2004/006961 | 1/2004 |
| WO | WO 2004/022078 | 3/2004 |
| WO | WO 2005/035742 | 4/2005 |
| WO | WO 2007/015252 | 2/2007 |
| WO | WO 2007/149861 | 12/2007 |
| WO | WO 2008/013863 | 1/2008 |
| WO | WO 2009/115581 | 9/2009 |
| WO | WO 2012/024573 | 2/2012 |
| WO | WO 2012/154301 | 11/2012 |
| WO | WO 2014/047067 | 3/2014 |

OTHER PUBLICATIONS

Baer, P. C. et al., Adipose-derived mesenchymal stromal/stem cells: tissue localization, characterization, and heterogeneity. *Stem Cells International*, Article ID 812693, 11 pages. Epub Apr. 12, 2012. (2012).

Bushkalova et al., Polyelectrolyte scaffolds for cardiac mesenchymal stem cell therapy. *Wound Repair and Regeneration*, 21(6): A59 (Nov.-Dec. 2013).

Hanson, S. E. et al., Clinical Applications of Mesenchymal Stem Cells in Soft Tissue Augmentation, *Aesthet Surg J.*, 30(6):838-842. (2010).

Hanson, S. E. et al., Mesenchymal Stem Cell Therapy for Nonhealing Cutaneous Wounds. *Plastic Reconstr. Surg.*, 125(2):510-516. (2010).

IAEA, Radiation sterilization of tissue allografts: Requirements for Validation and routine control—A code of practice, *IAEA*, Vienna. (2007). 65 total pages.

International Preliminary Report on Patentability for International Application No. PCT/US2012/029568, dated Sep. 24, 2013, 6 pages.

International Preliminary Report on Patentability for International Application No. PCT/US2013/060181, dated Mar. 24, 2015, 17 pages.

International Search Report and Written Opinion for International Application No. PCT/US2012/029568, dated Jul. 2, 2012, 7 pages.

International Search Report and Written Opinion for International Application No. PCT/US2013/060181, dated Dec. 4, 2013, 22 pages.

International Search Report and Written Opinion for International Application No. PCT/US2017/020492, dated May 31, 2017, 13 pages.

Iyer, S. S. et al., Anti-inflammatory effects of mesenchymal stem cells: novel concept for future therapies, *Expert Opin. Biol. Ther.*, 8(5):569-581. (2008).

Lim, J. S. et al., Effects of Adipose-derived Stromal Cells and of their Extract on Wound Healing in a Mouse Model, *J Korean Med Sci*, 25(5)746-751. (2010).

Office Action for U.S. Appl. No. 13/423,171, dated Mar. 18, 2014, 5 pages.

Office Action for U.S. Appl. No. 13/423,171, dated Sep. 10, 2013, 9 pages.

Office Action for U.S. Appl. No. 15/148,821, dated Jul. 7, 2016, 11 pages.

Office Action for U.S. Appl. No. 15/148,821, dated Sep. 8, 2016, 12 pages.

Office Action for U.S. Appl. No. 13/423,171, dated Apr. 24, 2013, 7 pages.

Peterson, D. et al., Sterile, freeze-dried microvascular tissue retains many benefits of stem cells. *ISSCR* Abstract, 2 total pages. (2013). [retrieved on May 7, 2019].

Peterson, D. et al., Sterile, freeze-dried microvascular tissue retains many benefits of stem cells. *ISSCR* Poster, 1 total page. (2013).

Peterson, D. et al., Sterile, lyophilized microvascular tissue retains many benefits of stem cells. *ISACB* Poster, 1 total page. (2014).

Peterson, D. et al., Sterilized, freeze-dried microvascular tissue retains many benefits of stem cells. *Cardiovascular Pathology: ISACB Abstracts From the 14th Biennial Meeting of the International Society for Applied Cardiovascular Biology*, 2 total pages. (2014).

Rosova, I. et al., Hypoxic preconditioning results in increased motility and improved therapeutic potential of human mesenchymal stem cells, *Stem Cells*, 26:2173-2182 (2008).

Supplementary European Search Report for European Application No. 16195005.0, dated Jan. 27, 2017, 9 pages.

Supplementary European Search Report for European Patent Application No. 12782247.6, dated Sep. 17, 2014, 9 pages.

Supplementary European Search Report for European Patent Application No. 13839621.3, dated Mar. 29, 2016, 8 pages.

Wang, E-T et al., Regulation of tissue repair and regeneration by electric fields. *Chinese Journal of Traumatology*. 13(1):55-61 (2010).

Whang, P.G. et al., Bone graft substitutes for spinal fusion. *Spine J.* 3:155-165. (2003).

Wierenga et al., Protection against radiation-induced damage to salivary glands by stem cell transplantation. *Blood*, 100(11) Abstract No. 4121. (Nov. 16, 2002).

Yew, T-L et al., Enhancement of wound healing by human multipotent stromal cell conditioned medium: the paracrine factors and p38 MAPK activation. *Cell Transplantation*, 20:693-706 (2011). Epub Dec. 2010.

Yoshimura, K. et al., Adipose-derived stem/progenitor cells: roles in adipose tissue remodeling and potential use for soft tissue augmentation. *Regenerative Medicine*, 4(2):265-273 (2009).

Zarandi, P. et al., Ps-43: Serum-free isolation of adipose tissue derived multipotent mesenchymal stromal cells. (Abstract), *Abstracts of the 6th Royan International Congress on Stem Stell Biology & Technology, Yakhteh Medical Journal*, 12(1): 41-42 (Summer 2010).

World Health Organization, "Second Global Consultation on Regulatory Requirements for Human Cells and Tissues for Transplantation: Towards Global Harmonization through Graduated Standards"; WHO Geneva, Jun. 7-9, 2006; 42 pages.

World Health Organization, "Aide-Memoire on Key Safety Requirements for Essential Minimally Processed Human Cells and Tissues for Transplantation"; WHO; 2006; 21 pages.

ALLOGENEIC MICROVASCULAR TISSUE FOR SOFT TISSUE TREATMENTS

CROSS-REFERENCE TO RELATED APPLICATION

This application is a continuation of U.S. patent application Ser. No. 14/698,763, filed Apr. 28, 2015 and issued as U.S. Pat. No. 10,137,224 on Nov. 27, 2018, which is a continuation of U.S. patent application Ser. No. 13/423,171, filed Mar. 17, 2012 and issued as U.S. Pat. No. 9,044,430 on Jun. 2, 2015, which claims priority to Provisional Application No. 61/454,367, filed Mar. 18, 2011, each of which is incorporated herein by reference in its entirety.

TECHNICAL FIELD

This application is directed to compositions and methods relating to tissue repair using allogeneic microvascular tissue or cells.

BACKGROUND

Tendon injuries are very common. Sprains will heal spontaneously, but complete tears will often lead to disability if not surgically treated. Despite surgical repairs, about 15% of Achilles tendons and 40% of two tendon rotator cuff repairs subsequently fail. Furthermore, the repaired tendons seldom return to pre-injury strength and function levels. Attempts to improve the success rate have involved better suture and bone anchors, new surgical methods, and patches to reinforce the repair and provide scaffolding for tissue ingrowth to thicken the tendon. There are also reports of improved tendon healing using growth factors such as BMP-2, BMP-12, PDGF-BB, and bFGF in preclinical models.

Although some researchers have indicated tendon as a possible tissue to grow using mesenchymal stem cells (MSC), very little work has been done along that line. There is even less work reported with adipose- or other microvascular tissue-derived stem or progenitor cells. It has been shown that fresh cells from adipose and other microvascular tissues could be used for regenerating orthopedic tissues. Others have since shown that these cells help treat tendon lesions in horse models of tendon injury, as well as other conditions. These cells were always autologous or syngeneic.

However, the use of autologous sourced stem cells is inconvenient. It requires two surgical procedures with associated pain, cost, and morbidity. There are also risks in shipping the tissue to the lab for processing and a delay in treatment of the injury or disease.

Recently bone graft products have been launched that use uncultured bone marrow cells from allogeneic donors adsorbed to bone chips or demineralized bone matrix (DBM). However, this type of product is unsuitable for soft-tissue repair and requires special handling to preserve the bone marrow cells.

SUMMARY

Embodiments of the described invention may include embodiments with one or more of the following features:

Use of allogeneic stem or progenitor cells for repair or regeneration of tendon, ligament, or skin.

Use of processed microvascular tissue for repair or regeneration of tendons, ligaments, or skin.

Use of allogeneic processed microvascular tissue for regeneration of tendons, ligaments, or skin.

Use of uncultured, dried allogeneic stem or progenitor cells to repair or regenerate bone, cartilage, tendon, ligaments, discs, or to reduce injury from an ischemic event in a human.

A processed microvascular tissue product which does not contain bone or bone matrix suitable for implantation into an allogeneic or xenogeneic recipient.

Manufacture of processed microvascular tissue from donors in a process validated to prevent viral contamination between lots.

Manufacture of processed microvascular tissue from donors in a process that uses a single enzyme, removes blood cells, or uses no enzyme.

A product suitable for implantation into a patient containing processed microvascular tissue which is stable at room temperature for more than a month.

A dried or lyophilized formulation of processed microvascular tissue.

A formulation comprising processed microvascular tissue dried at hyperbaric pressures.

The use of nonviable stem or progenitor cells for the repair or regeneration of bone, cartilage, tendon, ligaments, discs, or to reduce injury from ischemic events in people.

The use of allogeneic or xenogeneic nonviable stem or progenitor cells for the repair or regeneration of bone, cartilage, tendon, ligaments, discs, or to reduce injury from an ischemic event in a human.

The use of stem or progenitor cell products with less than 50% viability for the repair or regeneration of bone, cartilage, tendon, ligaments, discs, or to reduce injury from an ischemic event in a human.

The use of cryoperserved allogeneic microvascular tissue for the repair or regeneration of tendon or ligament.

A product suitable for implantation into a human patient comprising processed microvascular tissue with less than 50% viability.

A product suitable for implantation into a human patient comprising stem cells with stabilized membranes.

Combining allogeneic processed microvascular tissue with an orthopedic implant; a porous, flexible implantable scaffold; a surgical implant; pure water; porous coated implant; polymer solution; solvents such as DMSO, N-methylpyrrolidone (NMP), and alcohols; hydrogel; hyaluronic acid or other glycosaminoglycans or proteoglycans; collagen; fibrin; thrombin; blood clot; platelets; platelet rich plasma; demineralized bone matrix; or cancellous bone for implantation into a patient.

Combining allogeneic processed microvascular tissue with any of the following excipients: trehalose, sucrose, mannitol, or other sugars; glycols; DMSO; aldehydes; albumin.

Allogeneic or xenogeneic processed microvascular tissue for repair or regeneration of microvascular tissues other than bone in patients.

In an embodiment, a method is provided for repair or regeneration of a tissue (e.g., tendon, ligament, or skin) comprising applying a plurality of uncultured allogeneic stem or progenitor cells to the tissue and thereby effecting repair or regeneration of the tissue as compared to a control tissue to which uncultured allogeneic stem or progenitor cells are not applied. The plurality of uncultured allogeneic stem or progenitor cells can be included in a processed or cryopreserved microvascular tissue. The plurality of uncultured allogeneic stem or progenitor cells can include xenogeneic cells.

In some embodiments, a plurality of uncultured allogeneic stem or progenitor cells for use in a provided method can be less than 50% viable or can include substantially no viable cells.

In another embodiment, a method is provided for repair or regeneration of a tissue (e.g., tendon, ligament, bone, or skin) comprising applying a composition comprising substantially intact cell membranes of non-viable stem or progenitor cells to the tissue and thereby effecting repair or regeneration of the tissue as compared to a control tissue to which the composition is not applied. The non-viable stem or progenitor cells can be included in a processed or cryopreserved microvascular tissue.

In some embodiments, a composition for use in a provided method comprises less than 50% viable cells or can include substantially no viable cells.

In some embodiments, a composition for use in a provided method can be stable at room temperature and retains tissue healing activity for at least one month.

In some embodiments, a composition for use in a provided method can include non-viable stem or progenitor cells that have been dried or lyophilized.

In some embodiments, a composition for use in a provided method can include non-viable stem or progenitor cells have been treated to prevent microbial contamination.

In some embodiments, a composition for use in a provided method can further comprise an excipient or implantable scaffold.

In some embodiments, tissue healing activity in a provided method comprises improved healing of a soft or hard tissue exposed to the composition as compared to an analogous tissue similarly treated but without exposure to the composition.

In an embodiment, a composition is provided comprising a plurality of uncultured stem or progenitor cells formulated for implantation into an allogeneic or xenogeneic recipient, where the composition has tissue healing activity and includes no bone or bone-derived matrix.

In another embodiment, a composition is provided comprising substantially intact cell membranes of non-viable stem or progenitor cells formulated for implantation into an allogeneic or xenogeneic recipient, where the composition has tissue healing activity. In some embodiments, an internal component of the non-viable stem or progenitor cells can be included in the composition.

In some embodiments, a composition provided herein can allogeneic stem or progenitor cells that are included in a processed or cryopreserved microvascular tissue.

In some embodiments, a composition provided herein can include less than 50% viable cells. In some embodiments, a composition provided herein can include substantially no viable cells.

In some embodiments, a composition provided herein can be stable at room temperature and retain tissue healing activity for at least one month.

In some embodiments, the tissue healing activity of a composition provided herein comprises improved healing of a soft or hard tissue exposed to the composition as compared to an analogous tissue similarly treated but without exposure to the composition.

In some embodiments, a composition provided herein can include stem or progenitor cells that have been dried or lyophilized.

In some embodiments, a composition provided herein can further include an excipient or an implantable scaffold.

In some embodiments, a composition provided herein can include stem or progenitor cells that has been treated to prevent microbial contamination.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
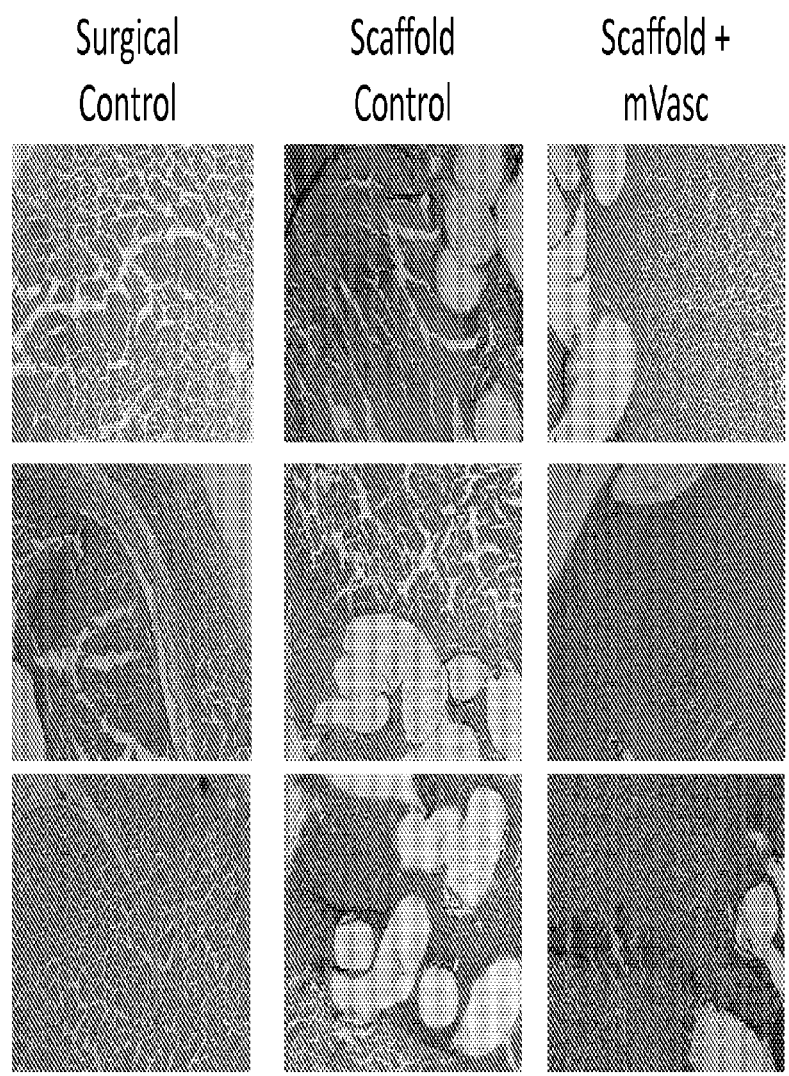
FIG. 1 shows hematoxylin and eosin (H & E) stains of Achilles tendon and associated tissue in surgical control, scaffold control, and scaffold plus microvascular tissue cell (mVasc) sample sections.

Described herein is a process that generates allogeneic (i.e., allogeneic or xenogeneic) processed or cryopreserved microvascular tissue which is ready to use off-the-shelf when needed. Also described is the use of processed or cryopreserved allogeneic microvascular tissue for soft tissue (e.g., tendon, ligament, skin) and hard tissue healing. The processed or cryopreserved microvascular tissue provided herein is minimally processed, uncultured microvascular tissue that includes a mixture of stem and/or progenitor cells produced from the dissociation (e.g., by enzymatic digestion) of a microvascular tissue (e.g., adipose, tendon, or muscle tissue). Processed or cryopreserved microvascular tissue can include additional molecules (e.g., whole or fragmented extracellular matrix molecules, growth factors, or cell surface molecules).

The term "processed microvascular tissue" as used herein refers to microvascular tissue that is dissociated as described herein, and then dried using, for example, a freeze-drying or spray drying technique. The term "cryopreserved microvascular tissue" as used herein refers to microvascular tissue that is dissociated as described herein, and then cryopreserved using known techniques. Processed microvascular tissue and cryopreserved microvascular tissue have soft and hard tissue healing (e.g., repair or regeneration) activity.

As used herein, "tissue healing activity" of a processed microvascular tissue is the ability of the provided processed microvascular tissue to facilitate improved healing (e.g., repair or regeneration) of a tissue (e.g., hard or soft tissue) exposed to the provided processed microvascular tissue as compared to an analogous tissue similarly treated but without exposure to a processed microvascular tissue. Improved healing is measured using any appropriate means, such as time to complete healing, amount of new tissue generated, strength of the resulting healed tissue, or functionality of the resulting healed tissue. Soft tissue includes tendons, ligaments, fascia, skin, fibrous tissues, fat, synovial membranes, muscle, nerves, and blood vessels. Soft tissue injuries that can benefit from the soft tissue healing activity of the provided processed microvascular tissues include, without limitation, injuries such as tendon and/or ligament tears and injuries resulting from ischemic events.

Allogeneic and xenogeneic stem cells have not previously been used to facilitate repair of soft tissues such as ligaments and tendons because of the difficulty of producing new soft tissue with autologous stem cells and the perception that allogeneic and xenogeneic stem cells will be rejected. In addition, the research on stem cell preservation by freeze drying has been done on purified hematopoietic stem cells in order to increase viability. In contrast, the process and composition described herein does not rely on purified stem cells or cell viability. Rather, the provided process is used to produce a processed or cryopreserved microvascular tissue containing a mixture of cells, including nonviable cells, mesenchymal stem and progenitor cells, and other molecules secreted by such cells (e.g., cytokines, growth factors, chemotactic molecules, and the like). In some embodiments, the processed or cryopreserved microvascular tissue contains a mixture of viable and nonviable cells.

Like autologous stem cell infusions, the allogeneic stem and/or progenitor cells in the provided processed or cryopreserved microvascular tissue do not persist long in a patient, but they trigger a cascade of responses in the patient that lead to improved healing. The processed or cryopreserved microvascular tissue described herein need not include viable or whole stem cells to induce improved soft tissue healing.

Processed or cryopreserved microvascular tissue described herein can be produced by dissociating a microvascular tissue. In some embodiments, the microvascular tissue is enzymatically digested using one or more enzymes. Suitable enzymes include those that contribute to cell dissociation, such as collagenases and neutral proteases. The enzymatic digestion process can be adjusted to increase or decrease cell dissociation. For example, if more complete cell dissociation is desired, more than one enzyme can be included or digestion time can be increased. While cell viability need not be maintained, in some embodiments it is generally desired that cellular membranes remain generally intact to preserve membranes containing attachment and signaling molecules even if some cell lysis occurs during enzymatic digestion. Thus, the use of enzymes such as lipidases may not be useful in such a process, according to one embodiment of the present invention.

Alternatively, the microvascular tissue can be dissociated without the use of enzymes. Rather, microvascular tissue can be dissociated using physical or chemical means, including the use of chelators, ultrasonic agitation, or mechanical cell dissociation.

The procurement of donor microvascular tissue and subsequent treatment can include steps for preventing microbial (e.g., bacterial, fungal, or viral) contamination. For example, donors can be screened for a predetermined list of microbial organisms (e.g., HIV, HPV, EBV, TB, etc.) prior to processing. Screening can be done using known techniques, such as detecting the presence of a microbial nucleic acid using polymerase chain reaction, or by detecting the presence of a molecule associated with a particular microbe by ELISA. Microbially contaminated microvascular tissue can be excluded from use, according to some embodiments of the present invention. In addition, processed or cryopreserved microvascular tissue can be produced using aseptic or sterile techniques.

Following tissue dissociation, microvascular tissue can be further treated to remove undesired cells or molecules, such as red blood cells, lipids, or adipocytes. Additional treatment will depend upon the source of microvascular tissue. For example, if the microvascular tissue source is adipose tissue, the dissociated microvascular tissue can be centrifuged at relatively low force to separate lipids, adipocytes, and some pre-adipocytes from the rest of the microvascular tissue. In other embodiments, known muscle cell isolation protocols, such as the use of density gradient centrifugation, may be used to further treat muscle tissue following enzymatic digestion to remove muscle cells and enrich for desired cells.

Once the microvascular tissue is prepared, it is preserved dried using a freeze-drying or spray-drying technique to produce processed microvascular tissue, or is cryopreserved. Any appropriate excipient can be used when preserving microvascular tissue, including sugars (e.g., trehalose, mannitol, sucrose), polyalcohols (e.g., polyethylene glycol), aldehydes, proteins (e.g., albumin), amino acids (e.g., glycine), surfactants (e.g., Tween 20), DMSO, and/or permanganates.

Freeze drying typically involves four steps: pretreatment, freezing, primary drying, and secondary drying. Pretreatment can include concentration adjustment or the addition of one or more excipients. Following pretreatment, the microvascular tissue is frozen. The freezing step is typically done in a carefully controlled manner (e.g., at a rate of cooling of between about $-0.5°$ C. per minute to about $-50°$ C. per minute) to preserve cell structure, however cell viability need not be preserved. In some embodiments, microvascular tissue is frozen at a rate of cooling of about $-10°$ C. per minute. The rate of cooling can be adjusted based on the particular microvascular tissue and excipients used. The microvascular tissue can be frozen using any appropriate means, including using mechanical refrigeration and/or exposing a container containing the microvascular tissue to dry ice or liquid nitrogen until it reaches a temperature suitable for freeze drying.

During the primary drying step, the temperature and pressure are adjusted to provide conditions suitable to cause sublimation of water from the microvascular tissue. The specific temperature and pressure can be adjusted to accommodate the excipient used and/or the concentration of the microvascular tissue.

During the secondary drying step, the temperature and pressure can be further adjusted to facilitate the removal of unfrozen water from the microvascular tissue. The final water content following the secondary drying step is preferably between 1% and 4% by weight, but can be adjusted in order to maximize shelf life or soft tissue healing activity.

In some embodiments, the microvascular tissue is spray dried. Prior to spray drying, the microvascular tissue can be pretreated similarly to microvascular tissue that is to be freeze dried, with the excipients being chosen as appropriate for spray drying rather than freeze drying. During spray drying, the microvascular tissue is atomized into droplets and exposed to heated air in a drying chamber.

In some embodiments, microvascular tissue is not processed by drying, but cryopreserved. Methods for cryopreserving tissue are known. For example, microvascular tissue is mixed with one or more excipients (e.g., DMSO) and cooled in a carefully controlled manner. In some embodiments, cooling is done in two or more stages in which the first stage is done in a controlled manner (e.g., reducing the temperature by 1° C. per minute) to an intermediate temperature (e.g., −30° C.), with the second stage transferring cells at the intermediate temperature to a colder storage temperature (e.g., −196° C.).

Cryopreserved microvascular tissue is stored at a temperature suitable for maintaining the cryopreserved state (e.g., from about −30° C. to −196° C.). Freeze dried or spray dried processed microvascular tissue can be stored in a wider variety of conditions than cryopreserved cells, live cells, or fresh tissue. Suitable temperatures for the storage for processed microvascular tissue include temperatures from about −100° C. to about 45° C. In some embodiments, freeze dried or spray dried processed microvascular tissue can be stored at room temperature. The shelf life of the provided processed microvascular tissue is at least one week, and preferably, at least one month, while maintaining tissue healing activity.

Additionally, because viability is not required for suitability of the processed or cryopreserved microvascular tissue for use in soft tissue repair, the preservation process and storage need not be adjusted to maintain viability. The percentage of viable cells in the provided microvascular tissue before processing or cryopreservation can be up to 100%. After processing or cryopreservation, it is less than 50%, e.g., less than 40%, less than 30%, less than 20%, or less than 10%. In some embodiments, the provided processed microvascular tissue contains no viable cells after processing or cryopreservation.

Further provided are methods of using processed microvascular tissue. Processed microvascular tissue can be applied directly to a tissue in need of repair, or can be applied to tissue surrounding such a tissue in need of repair. In some embodiments, a dried processed microvascular tissue is reconstituted in a suitable carrier (e.g., water or saline) and directly applied to a tissue in need of repair. In some embodiments, reconstituted processed microvascular tissue is applied to a scaffold, such as a collagen matrix or biocompatible fabric, prior to being applied to a tissue. In other embodiments, a processed microvascular tissue is used to coat a material, such as a flexible biocompatible scaffold (e.g., woven or nonwoven fabric sheets or thread), biocompatible microbeads or particles, or an implantable medical device. Spray dried processed microvascular tissue is particularly suited to coating a material comprising microbeads or particles without requiring reconstitution prior to coating, as coating can be done during the spray drying process.

Processed or cryopreserved microvascular tissue can be combined with any suitable device or material prior to implant into a patient. Processed or cryopreserved microvascular tissue can be combined with an orthopedic implant; a porous, flexible implantable scaffold; a surgical implant; pure water; saline; a porous coated implant; polymer solution; solvents such as DMSO, N-methylpyrrolidone (NMP), and alcohols; hydrogel; hyaluronic acid or other glycosaminoglycans or proteoglycans; collagen; fibrin; thrombin; blood clot; platelets; platelet rich plasma; demineralized bone matrix; autologous cells; and/or cancellous bone.

Processed or cryopreserved microvascular tissue can be packaged alone for example, in a vial, or in combination with other products, such as those listed as being suitable for combination with processed or cryopreserved microvascular tissue. When packaged with another material, the processed or cryopreserved microvascular tissue can be separately packaged, or premixed or associated with the other material. In some embodiments, processed microvascular tissue is packaged as a coating on a biocompatible material.

The following examples are meant to illustrate specific embodiments, and are not intended to limit the scope of the invention.

EXAMPLES

Example 1. Preparation of Lyophilized Microvascular Tissue

Preparation of Microvascular Tissue Cells

Rat microvascular tissue was prepared from epididymal fat pads or inguinal fat pads. Briefly, Worthington collagenase (lot #4145) was put into solution in phosphate buffered saline at 1 mg/ml, resulting in a solution with a specific activity of 40 U/ml. This collagenase solution was applied to the fat (inguinal and epididymal pads were processed separately) in an equal volume to weight ratio and incubated at 4° C. for 45 minutes while mixing. Collagenase activity was stopped with 25% bovine serum albumin and the cells were spun down. As assessed by trypan blue exclusion, cells collected from epididymal fat pads had a viability of about 75%, while cells collected from inguinal fat pads had a viability of about 80%. The cells were resuspended and counted. Epididymal fat yielded about 720,000 cells per ml, and inguinal fat yielded about 215,000 cells per ml.

Human microvascular tissue can be prepared using lipoaspirate that is enzymatically treated in a similar manner as the rat microvascular tissue.

Lyophilization of Microvascular Tissue Cells

The collected cells were prepared for lyophilization in preservation medium (6.8% trehalose, 2% Hetastarch, 5% albumin, and 1 unit/ml heparin), and placed into glass vials with stopper closures and crimp seals suitable for lyophilization. To lyophilize the cells, the lyophilizer temperature was dropped from 23° C. to −45° C. at a rate of 2.5° C. per minute. Temperature was held at −45° C. for 3 hours, followed by a first drying step. During the first drying step, temperature was increased from −45° C. to −35° C. at a rate of 2.5° C. per minute and the pressure was reduced to 80 torr, where the temperature and pressure were held for 36 hours. A secondary drying step was then performed by increasing the temperature from −35° C. to −5° C. at a rate of 0.2 C per minute, then held at 5° C. for 6 hours. Following the second drying step, the vials were stoppered and crimp sealed under nitrogen.

Viability Assessment of Microvascular Tissue Cells

Two days after lyophilization, the cells were rehydrated and initial cell viability was assessed by trypan blue exclusion. Cell metabolic function was assessed by measuring alamarBlue® (Life Technologies, Carlsbad, Calif.) metabolism according to the manufacturer's instructions. Rehydrated cells were incubated in M3:10™ medium (Incell, San Antonio, Tex.) supplemented with 10% fetal bovine serum in a T-25 flask at 37° C. for 7 days to assess proliferation ability.

Following rehydration, the general structure of the cells appeared to be maintained in 5-25% of cells, with a more exact calculation being difficult due to the appearance of many broken cells. The cells had an initial viability of less than 1-2%, with few cells retaining the ability to exclude trypan blue. The morphology of those cells maintaining the ability to exclude trypan blue suggested they were undergoing apoptosis, displaying enlarged nuclei and nuclear and cytoplasmic blebbing. No significant ability to metabolize alamarBlue® was observed, indicating that metabolic integrity of the lyophilized cells was not maintained. None of the cells were able to establish a culture in M3:10™ medium, confirming low/no viability of the lyophilized cells.

Example 2. Treatment of Tendon Damage Using Cryopreserved Microvascular Tissue

Preparation of Cells from Microvascular Tissue

Microvascular tissue cells were prepared from rat epididymal fat pads as described in Example 1. The cells were cryopreserved by resuspending the cells in M3DEF defined medium without supplements (Incell), adding an equal volume of EZ-CPZ (Incell), with a final DMSO concentration of 5%. The cells were then frozen slowly in vials in a slow cool box overnight at −80° C. and then transferred to −130° C. Viability of the cryopreserved cells was determined to be less than 50% as assessed using trypan blue exclusion. Viability was typically around 90% before preparation.

Preparation of Microvascular Tissue Cell-Impregnated Scaffold Material

BioFiber® Collagen-coated Scaffold material (Tornier) was placed on top of thick gauze material resting in PBS. The scaffold material was pre-wet with PBS prior to addition of microvascular tissue cells.

The cells were thawed quickly at 37° C., centrifuged at 400×g for 5 minutes, and resuspended at 1×10$^6$ cells per ml in phosphate buffered saline (PBS). The suspended cells were applied to the pre-wet scaffold material at a rate of 100 μl of the suspended cells per cm$^2$ of scaffold material, and allowed to absorb into the scaffold material by wicking action of the gauze beneath the scaffold material.

Scaffold material was kept moist using PBS, and allowed to incubate for 15-20 minutes at 37° C. and 5% $CO_2$ in a humid chamber. Microvascular tissue cell-impregnated scaffold material was kept moist and under aseptic conditions until use in Achilles tendon model.

Achilles Tendon Damage Model

Prior to treatment, 32 animals were weighed and randomly assigned to 4 treatment groups. The right rear limb of each animal was shaved one day prior to the start of the test. Prior to surgery on Day 1, animals were weighed and anesthetized with an intramuscular injection of ketamine hydrochloride 100 mg/mL (40-90 mg/kg) and xylazine 100 mg/mL (5-10 mg/kg). Mask or chamber induction with Isoflurane may also be used. The skin was surgically prepared with betadine and alcohol scrubs, and draped using aseptic surgical techniques.

Microvascular tissue cell-impregnated scaffold material was prepared immediately prior to implantation. The graft was trimmed to 10 mm×11 mm and two of the corners were notched. Two 5-0 polypropylene sutures were placed in the graft for fixation. The graft was then rolled to form a cylindrical structure for wrapping around the Achilles tendon. The graft was set aside in the Petri dish with saline and covered until used.

A straight, lateral skin incision was made from the caudal (distal) tibia of the right rear limb to the level of the mid tibia. The skin was dissected and refracted to allow a lateral exposure of the Achilles tendon from calcaneus to its musculo-tendinous junction. The exposed Achilles tendon was slightly abraded with mouse-tooth forceps prior to graft test article placement. A single 0.5 mm drill hole was made in the lateral to medial direction through the calcaneus to allow suture passage for graft fixation. The implant area was irrigated with saline to remove any debris and blotted dry.

The graft was removed from the saline and then wrapped around the Achilles tendon with the notched ends adjacent to the calcaneus. The graft edge was closed with interrupted 5-0 polypropylene sutures. The cranial graft fixation suture was placed in the gastrocnemius cranial to the musculo-tendinous junction using a modified Mason-Allen suture pattern. The caudal graft fixation suture was then passed through the drill hole in the calcaneus and tensioned with the foot in a neutral position and tied. Six suture knots were tied for all fixation sutures. The incision was closed in a layered fashion using appropriate suture material. The incision site was observed evaluated daily until day 10 post operation.

The rats were grouped into the treatment groups outlined in Table 1.

TABLE 1

Treatment Groups

| Group | No. | Treatment |
|---|---|---|
| Surgical control | 8 | Achilles tendon will be slightly abraded with mouse-tooth forceps |
| Scaffold control | 8 | Achilles tendon will be slightly abraded with mouse-tooth forceps + Tornier's BioFiber Scaffold Coated with Collagen |
| Scaffold + microvascular tissue cells (mVasc) | 8 | Achilles tendon will be slightly abraded with mouse-tooth forceps + Tornier's BioFiber Scaffold Coated with Collagen + Rat microvascular tissue cells (thawed) |

Tissue Processing

Rats were euthanized at day 42±1. Immediately following euthanasia, the implanted test or control article sites and surrounding tendinous tissue were collected by excision from each animal. All collected samples were split in half. One-half of the collected tissue was stored in 10% neutral buffered formalin for routine histopathological and immunohistochemistry evaluation. The remaining half was snap frozen at ≤−70° C. in liquid nitrogen for gene expression analysis. A section of tendon and liver of each animal was also collected as staining controls and stored in 10% neutral buffered formalin for immunohistochemistry evaluation.

Histopathological, immunohistochemical, and gene expression analysis was done by BioModels (Watertown, Mass.). Briefly, hematoxylin and eosin and trichrome stains were performed on the tissues stored in 10% neutral buffered formalin. Immunohistochemistry utilizing anti-tenascin antibodies was also performed on the tissues stored in 10% neutral buffered formalin and on the tissues collected as staining controls. The tissues snap frozen at ≤−70° C. were utilized for isolation of RNA and qPCR of tenascin. Tenascin is a marker for tenocyte progenitor cells.

Results

Figure 2:
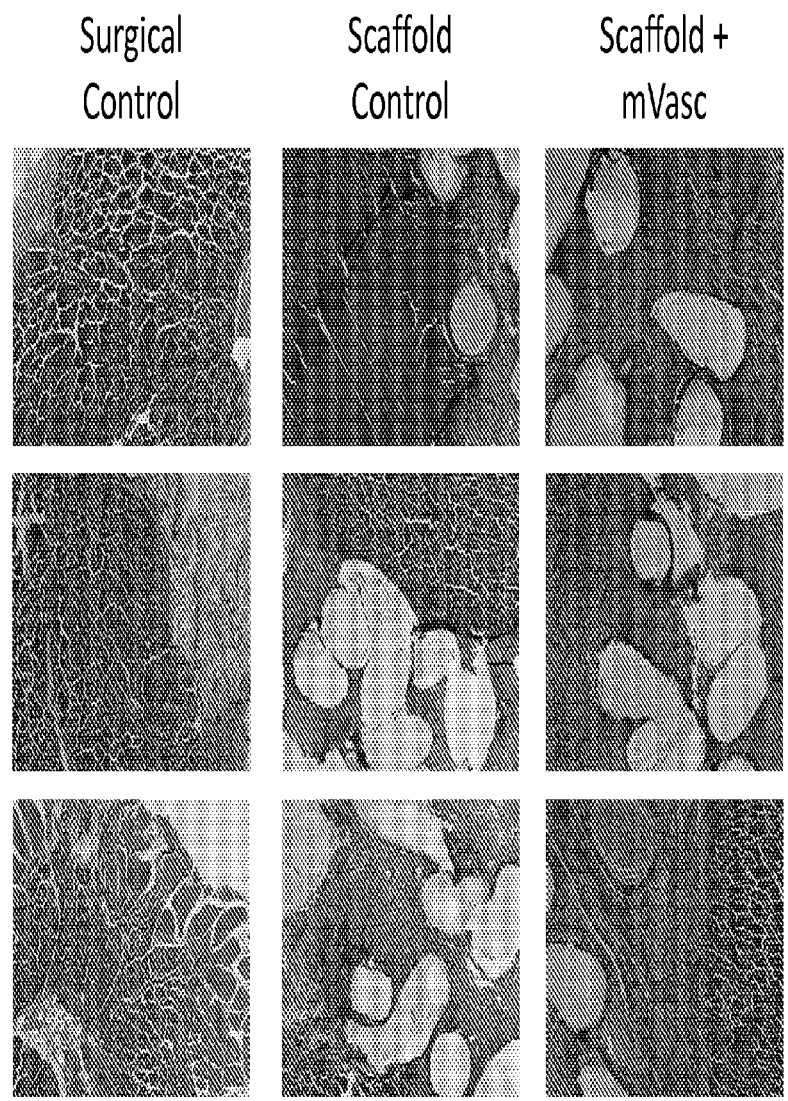
FIG. 2 shows trichrome stains of Achilles tendon and associated tissue in surgical control, scaffold control, and scaffold plus microvascular tissue cell (mVasc) sample sections.

Surgical controls showed normal histology in all but one animal, which demonstrated cellular invasion and loss of fascicular structure. This is commonly seen in tendons that have been treated surgically. Examples of H & E stains of tendon and associated tissue in surgical control sample sections are shown in the left column of FIG. 1. Examples of trichrome stains of tendon and associated tissue in surgical control sample sections are shown in the left column of FIG. 2.

Rats receiving scaffolds with no microvascular tissue cells showed tissue invasion into the scaffolds. The associated tendons in the scaffold controls showed normal structure in 6 of 8 animals. Two of the scaffold control animals showed inflammation, which may have resulted from infections and/or wound dehiscence. Examples of H & E stains of tendon and associated tissue in scaffold control sample sections are shown in the center column of FIG. 1. Examples of trichrome stains of tendon and associated tissue in scaffold control sample sections are shown in the center column of FIG. 2.

Figure 3:
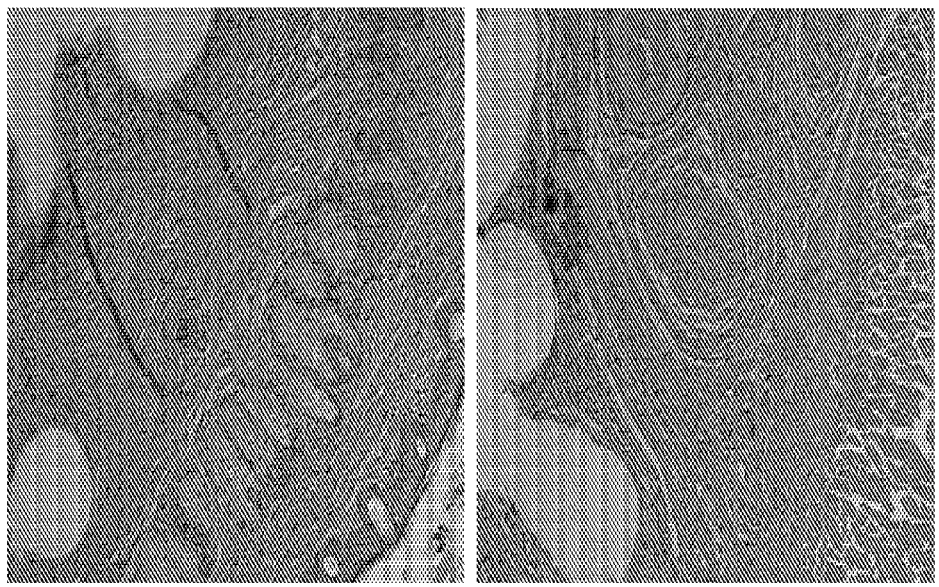
FIG. 3 shows H & E stains of Achilles tendon and associated tissue in scaffold plus microvascular tissue cell sample sections, showing skin-like structures grown into the scaffold.
Figure 4:
FIG. 4 shows a trichrome stain of Achilles tendon and associated tissue in a scaffold plus microvascular tissue cell sample section, showing bone-like structure grown into the scaffold where it was attached to the calcaneus.

Rats receiving scaffold plus microvascular tissue cells also displayed tissue invasion into the scaffolds. The associated tendons showed normal structure in 6 of 7 animals and cellular invasion in 1 of 7. In 5 of 7 of the animals, tendon approximated the cell-loaded scaffolds, and the appearance of new tendon formation was evident in 4 of 7 animals. Examples of H & E stains of tendon and associated tissue in scaffold plus microvascular tissue cell sample sections are shown in the right column of FIG. 1. Examples of Masson's trichrome stains of tendon and associated tissue in microvascular tissue cell sample sections are shown in the right column of FIG. 2. One of the rats exhibited inflammation and one animal showed bone ingrowth into the scaffold (FIG. 4). In two of the rats with scaffold plus microvascular tissue cells, skin appeared to have grown in the vicinity of the scaffold (FIG. 3), suggesting enhanced skin regeneration.

Figure 5:
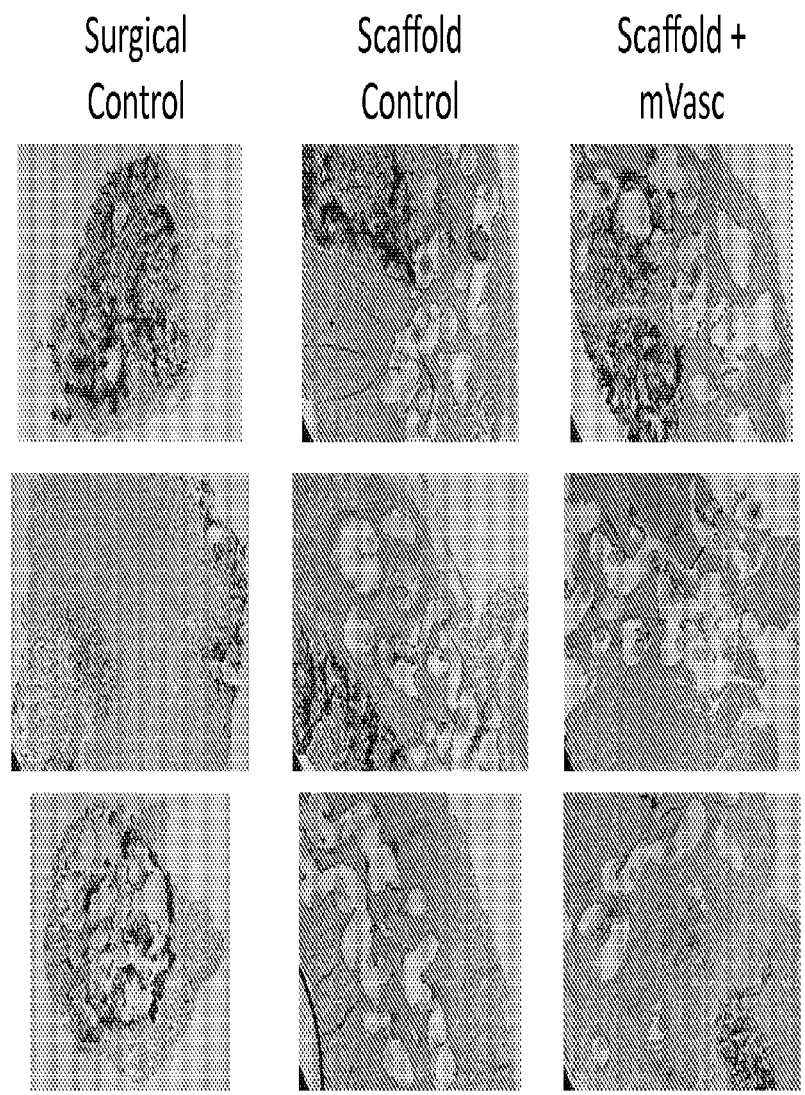
FIG. 5 shows immunohistochemical staining of tenascin expression in Achilles tendon and associated tissue in surgical control, scaffold control, and scaffold plus microvascular tissue cell (mVasc) sample sections.

Quantitative PCR analysis for tenascin determined tenascin expression levels to be 3.9-fold and 7.4-fold higher than surgical controls in the scaffold control and scaffold plus microvascular tissue cells, respectively (absolute values, 2.3, 8.9, and 17.0 for surgical controls, scaffold controls, and scaffold plus microvascular tissue cells, respectively). Immunohistochemical staining also showed an increase of tenascin expression in scaffold plus microvascular tissue cells (FIG. 5, right column).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A composition comprising a plurality of dissociated and then dried stem or progenitor cells,
    wherein the plurality of stem or progenitor cells contains less than 30% viable cells,
    wherein the composition has tissue healing activity,
    wherein the plurality of stem or progenitor cells has intact cell membranes, and
    wherein the plurality of stem or progenitor cells has been lyophilized.

2. The composition of claim 1, wherein the plurality of stem or progenitor cells comprises no viable cells.

3. The composition of claim 1, wherein the plurality of stem or progenitor cells has been spray-dried.

4. The composition of claim 1, wherein the plurality of stem or progenitor cells is xenogeneic to a recipient.

5. The composition of claim 1, wherein the plurality of stem or progenitor cells is allogeneic to a recipient.

6. The composition of claim 1, wherein the plurality of stem or progenitor cells is further treated to remove undesired cells or molecules.

* * * * *